(12) United States Patent
Hollopeter et al.

(10) Patent No.: US 11,484,382 B2
(45) Date of Patent: Nov. 1, 2022

(54) SYSTEM AND METHOD FOR IDENTIFICATION OF ILLUMINATION ABNORMALITIES AND AUTOMATIC COMPENSATION THEREFOR

(71) Applicant: American Sterilizer Company, Mentor, OH (US)

(72) Inventors: Michael Hollopeter, Kirtland, OH (US); Ian Hugh Cook, Miami, FL (US)

(73) Assignee: American Sterilizer Company, Mentor, OH (US)

( * ) Notice: Subject to any disclaimer, the term of this patent is extended or adjusted under 35 U.S.C. 154(b) by 652 days.

(21) Appl. No.: 16/393,168

(22) Filed: Apr. 24, 2019

(65) Prior Publication Data

US 2020/0337797 A1 Oct. 29, 2020

(51) Int. Cl.
*A61B 90/00* (2016.01)
*H05B 47/175* (2020.01)
(Continued)

(52) U.S. Cl.
CPC .............. *A61B 90/36* (2016.02); *G01S 17/08* (2013.01); *H05B 47/105* (2020.01); *H05B 47/175* (2020.01)

(58) Field of Classification Search
CPC ......... A61B 90/36; A61B 1/06; A61B 1/0607; A61B 1/0615; A61B 1/0623; A61B 1/063; G01S 17/08
(Continued)

(56) References Cited

U.S. PATENT DOCUMENTS 6,880,957 B2    4/2005   Walters
6,964,490 B2   11/2005   Scholz
(Continued)

FOREIGN PATENT DOCUMENTS

CN    CN 204681641 U    9/2015
CN        105953140 A    9/2016
(Continued)

OTHER PUBLICATIONS

International Search Report from corresponding International Patent Application No. PCT/US2020/029426 dated Jul. 30, 2020.
(Continued)

*Primary Examiner* — Si Ming Ku
(74) *Attorney, Agent, or Firm* — Kusner & Jaffe

(57) ABSTRACT

A system for identification of abnormalities related to illumination of a target and automatic compensation therefor includes a lighthead and a controller. The lighthead is configured to illuminate the target. The lighthead includes a plurality of lighting modules configured to emit light therefrom. Each of the lighting modules includes a distance sensor configured to measure a distance from the lighting module to a surface toward which the lighting module is pointed. The controller is configured to identify one or more abnormalities of the measured distances, determine a true distance from the lighthead to the target based on the measured distances, predict an amount of illumination based on the true distance that would be supplied to the target without the identified abnormalities, and compensate for the identified abnormalities by respectively adjusting an amount of light emitted from the lighting modules to illuminate the target according to the predicted amount of illumination.

14 Claims, 5 Drawing Sheets

(51) Int. Cl.
　　　H05B 47/105　　(2020.01)
　　　G01S 17/08　　(2006.01)
(58) Field of Classification Search
　　　USPC .......................................................... 600/249
　　　See application file for complete search history.

(56) References Cited

U.S. PATENT DOCUMENTS

| | | |
|---|---|---|
| 7,224,472 B2 | 5/2007 | Bauch et al. |
| 7,706,683 B2 | 4/2010 | Rossner et al. |
| 8,292,804 B2 | 10/2012 | Marka et al. |
| 8,710,415 B2 | 4/2014 | Peyras |
| 9,504,113 B2 | 11/2016 | Sattler et al. |
| 9,629,220 B2 | 4/2017 | Panopoulos et al. |
| 10,544,921 B2 * | 1/2020 | Li ........................ F21V 23/0471 |
| 2017/0296291 A1 * | 10/2017 | Bärlund .................. G09F 19/18 |
| 2017/0325319 A1 | 11/2017 | Schmid et al. |

FOREIGN PATENT DOCUMENTS

| | | |
|---|---|---|
| CN | 106500017 A | 3/2017 |
| EP | 3 231 390 A1 | 10/2017 |
| WO | WO 2005/012997 A2 | 2/2015 |
| WO | WO-2018/203881 A1 | 11/2018 |

OTHER PUBLICATIONS

Written Opinion of the International Searching Authority from corresponding International Patent Application No. PCT/US2020/029426 dated Jul. 30, 2020.

\* cited by examiner

SYSTEM AND METHOD FOR IDENTIFICATION OF ILLUMINATION ABNORMALITIES AND AUTOMATIC COMPENSATION THEREFOR

FIELD OF THE INVENTION

The present invention relates generally to a system and method for identification of illumination abnormalities and automatic compensation therefor. More particularly, the present invention relates to a system and method for identifying a true distance between a lighthead and a target and automatically compensating for abnormalities in illumination of the target based on the identified true distance.

BACKGROUND OF THE INVENTION

In general, light sources are operated to illuminate a target. However, it is relatively common for environmental abnormalities to affect the illumination of the target. These environmental abnormalities may include, but are not limited to, a blockage that occurs between the light source and the target or an incorrect positioning of the light source relative to the target.

For example, in a surgical environment, a surgical staff member might move between an area of a lighthead and an area of a surgical work surface, thereby blocking the area of the lighthead and inhibiting light emitted from the blocked area of the lighthead from reaching the corresponding area of the surgical work surface. In another example, a surgical staff member might move the surgical work surface to a different location that no longer corresponds to the positioning of one or more areas of the lighthead.

Many systems have been developed to identify such abnormalities and automatically adjust the intensity or the location of the light emitted from a light source to maintain a desired luminance of an illuminated target. Such identification systems have been known to employ proximity sensors or coordinate referencing cameras. Closed loop luminance sensors, such as photodiodes or CCD cameras, have also been used to sense variances from optimal target luminance.

In such systems that incorporate a lighthead as the light source, the sensor input is communicated to a controller. The controller compensates for the sensed abnormalities by adjusting either the positioning of light modules in the lighthead to avoid the abnormalities or an intensity of light being emitted from the light modules to compensate for the abnormalities. In the latter case, when an abnormality is detected that blocks light emitted from a particular light module from reaching a target, the intensity of light emitted from the affected light module may be reduced while the intensity of light emitted from adjacent unaffected light modules may be increased to compensate for the abnormality.

The present invention provides an improved system and method of identifying abnormalities between a light source and an illumination target, such as light blockages and erroneous positioning, and compensating for those abnormalities. The present invention accomplishes this through the determination of the true distance between the light source and the illumination target and compensating for the abnormalities detected in the course of the true distance determination.

SUMMARY OF THE INVENTION

In accordance with the present invention, there is provided a system for identification of abnormalities related to illumination of a target and automatic compensation therefor. The system includes a lighthead and a controller. The lighthead is configured to illuminate the target. The lighthead includes a plurality of lighting modules configured to emit light therefrom. Each of the lighting modules includes a distance sensor configured to measure a distance from the lighting module to a surface toward which the lighting module is pointed. The controller is configured to identify one or more abnormalities of the measured distances, determine a true distance from the lighthead to the target based on the measured distances, predict an amount of illumination based on the true distance that would be supplied to the target without the identified abnormalities, and compensate for the identified abnormalities by respectively adjusting an amount of light emitted from the lighting modules to illuminate the target according to the predicted amount of illumination. The abnormalities of the measured distances respectively indicate that the surfaces toward which the lighting modules related to the abnormalities are pointed are not surfaces of the target In accordance with another embodiment of the present invention, there is provided a method for identification of abnormalities related to illumination of a target and automatic compensation therefor. The method includes measuring a distance from each of a plurality of lighting modules of a lighthead to a surface toward which the lighting module is pointed. The method also includes identifying, via a controller, one or more abnormalities of the measured distances. The method further includes determining, via the controller, a true distance from the lighthead to the target based on the measured distances. The method additionally includes predicting, via the controller, an amount of illumination based on the true distance that would supplied to the target without the identified abnormalities. The method still further includes compensating, via the controller, for the identified abnormalities by respectively adjusting an amount of light emitted from the lighting modules to illuminate the target according to the predicted amount of illumination. The abnormalities of the measured distances respectively indicate that the surfaces toward which the lighting modules related to the abnormalities are pointed are not surfaces of the target.

An advantage of the present invention is to provide automatic detection of an abnormality that comes between an illumination target and a lighting module of a lighthead pointed at the target.

Another advantage of the present invention is to provide such automatic detection without the need of photosensors and lighting filters to adjust for environmental conditions impacting the readings taken by the photosensors.

A further advantage of the present invention is to provide automatic detection of when a lighting module of the lighthead is not pointed toward the illumination target.

Still another advantage of the present invention is to determine a true distance of the lighthead to the illumination target and predict an amount of light required for illumination of the target based on the true distance.

These and other advantages will become apparent from the following description of illustrated embodiments taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF THE INVENTION

Figure 1:
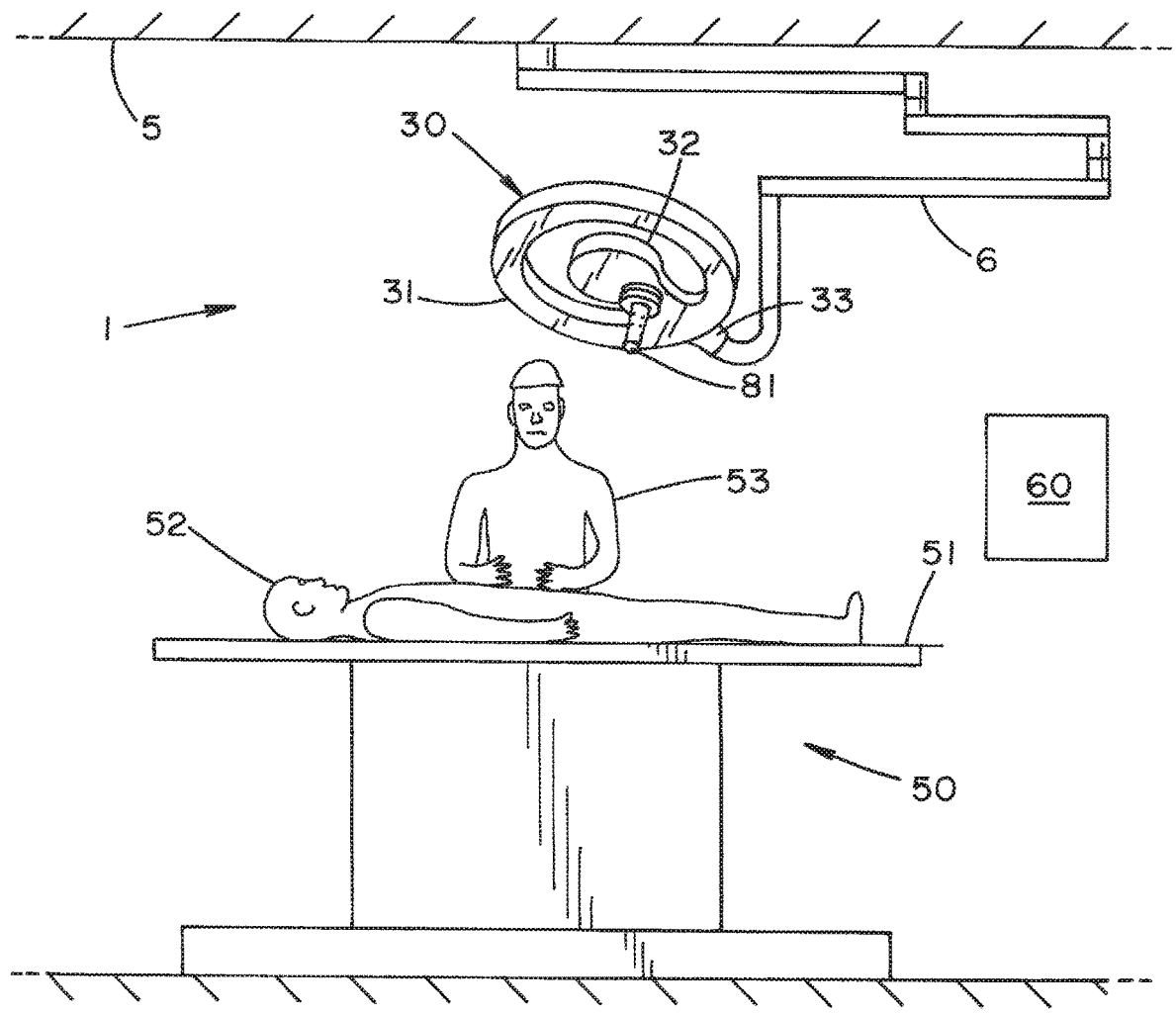
FIG. 1 is a plan view of an example surgical environment according to a first embodiment of the present invention that includes a lighting system.

Referring now to the drawings wherein the showings are for the purposes of illustrating an embodiment of the invention only and not for the purposes of limiting same, FIGS. 1-4 illustrate an example implementation of a lighting system in a surgical environment 1 in which a surgical table 50 is positioned.

The lighting system includes a lighthead 30 and a controller 60. The lighthead 30 is configured to illuminate a target. In this example implementation, the illumination target is a work surface 51 of the surgical table 50 on which a surgical patient 52 is positioned to enable a surgical staff member 53 to perform a surgical operation thereon. The controller 60 may be a conventional microprocessor-based computer system that is in communication with various accessory devices of the lighting system, including the lighthead 30. The controller 60 is equipped to receive and analyze data from the lighthead 30 and control operation of the lighthead 30 according to the analyzed data.

As is illustrated in FIG. 1, the lighting system may also include a support assembly 6 depending on the configuration and the implementation of the lighting system. The support assembly 6 supports the lighthead 30 from a ceiling 5 of an area containing the surgical environment 1 and is adjustable to allow desired positioning of the lighthead 30 within the surgical environment 1. The support assembly 6 may take the form of a conventional suspension system, which may include, but is not limited to, a plurality of suspension arms, hubs, mounts, and yokes.

Figure 2:
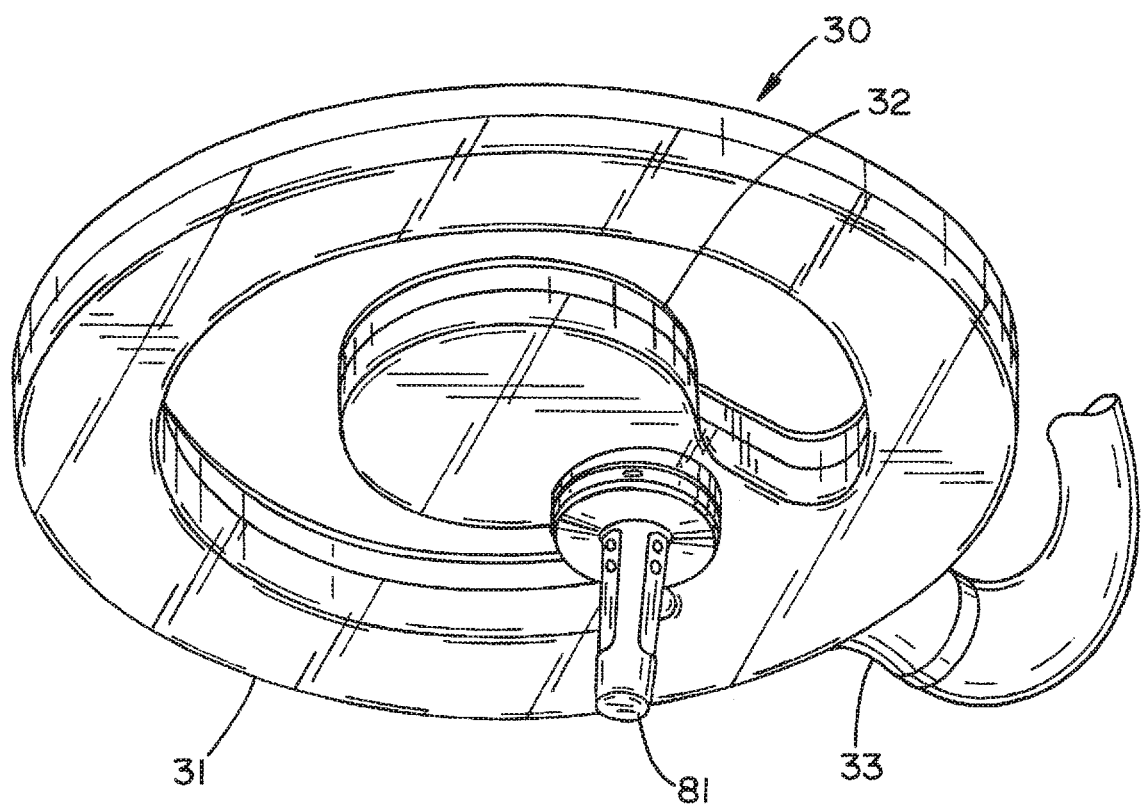
FIG. 2 is a plan view of a lighthead of the lighting system according to a first embodiment of the present invention.
Figure 3:
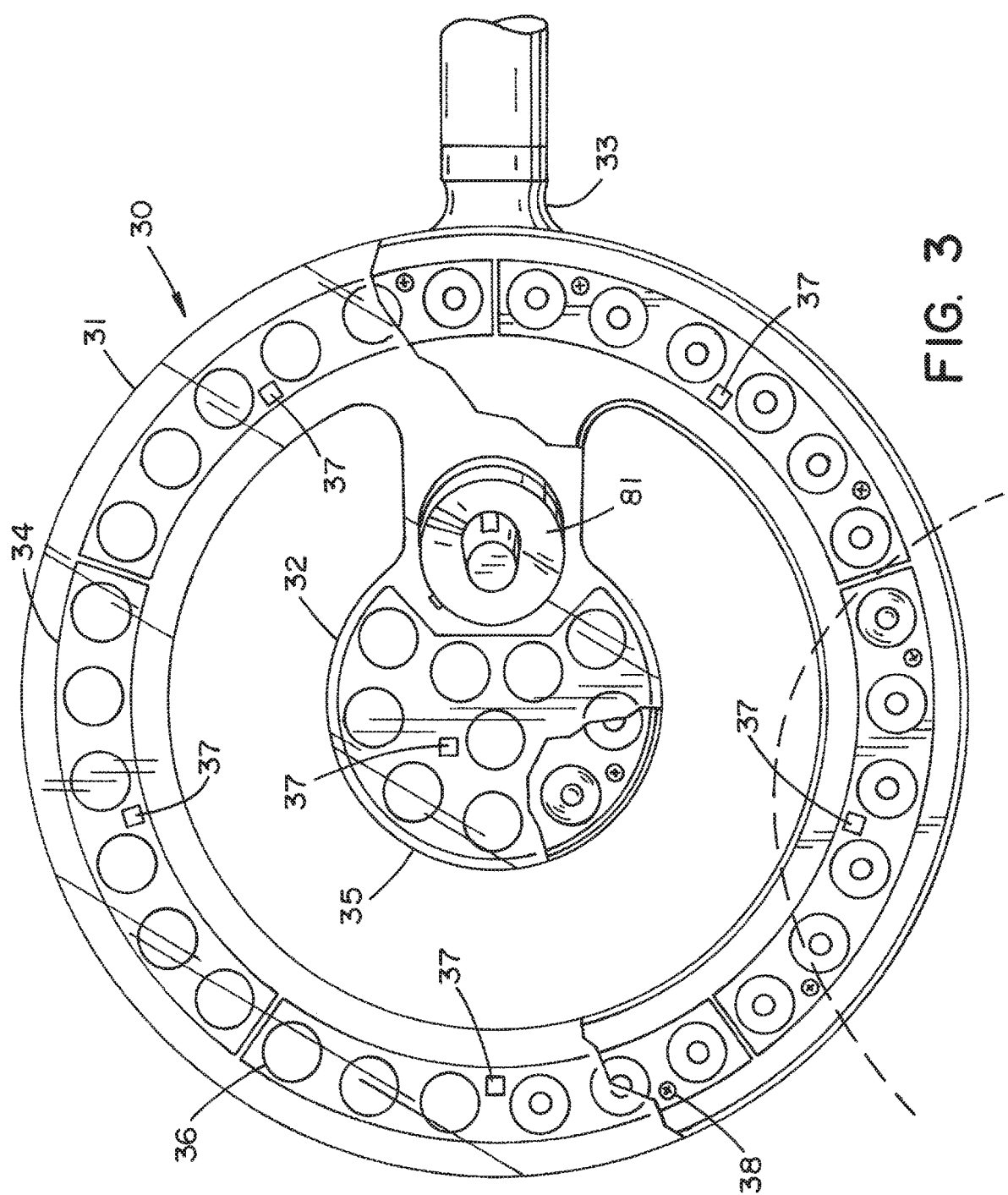
FIG. 3 is a front view of the lighthead of the lighting system according to the first embodiment of the present invention.
Figure 4:
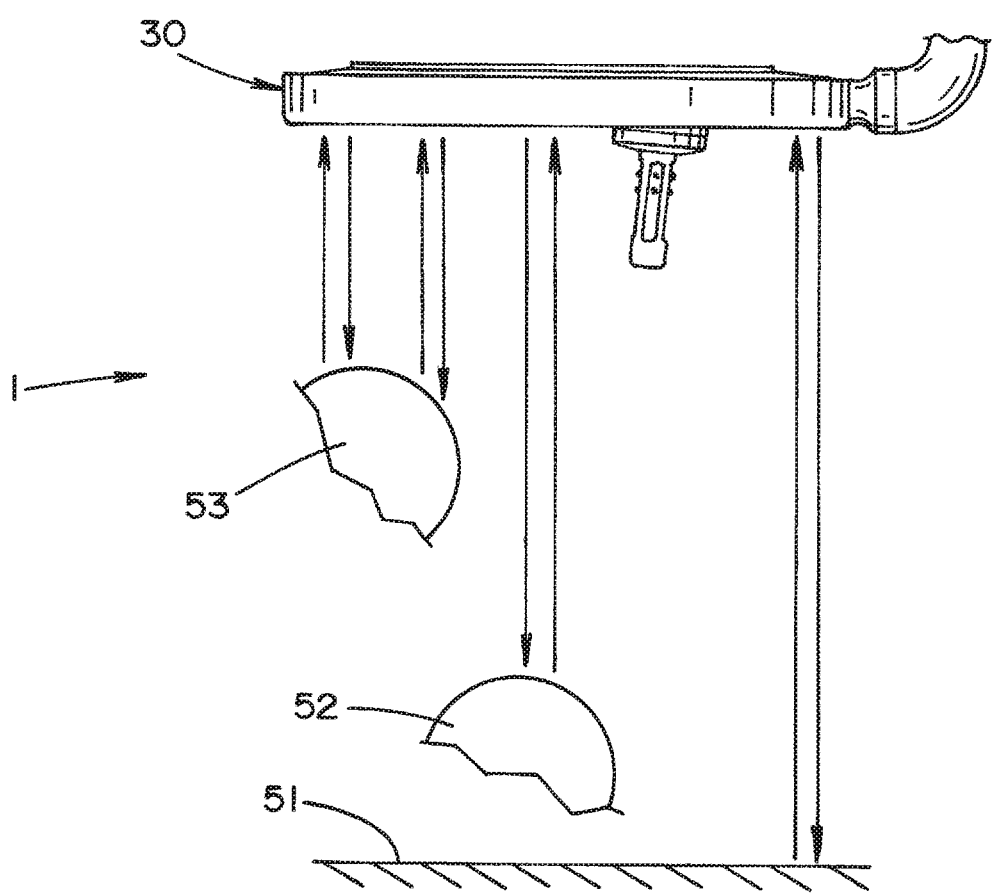
FIG. 4 is a plan view of the surgical environment according to the first embodiment of the present invention, in which an abnormality is positioned between lighting modules of the lighthead to an illumination target.

As is illustrated in FIGS. 2-4, the lighthead 30 includes an outer ring 31, a central hub 32, a neck 33, and a handle 81. The outer ring 31 corresponds with a perimeter of the lighthead 30 and surrounds the central hub 32. The neck 33 connects the outer ring 31 to the central hub 32. The handle 81 is mounted on the central hub 32. The handle 81 can be grasped by the surgical staff member 53 to manually adjust the positioning of the lighthead 30. The handle 81 may also include control mechanisms by which the surgical staff member 53 can control the lighting provided by the lighthead 30.

While the lighting system may be comprised of only the lighthead 30, the controller 60, and the support assembly 6, embodiments described herein are not limited thereto. For example, the lighting system may be comprised of several lightheads and support assemblies respectively positioned throughout areas of the surgical environment 1. Other lightheads and support assemblies may also be positioned on walls of the surgical environment 1 that are not illustrated herein.

In FIG. 1, the controller 60 is illustrated as being mounted in a location within the surgical environment 1. However, embodiments disclosed herein are not limited thereto. For example, the controller 60 may be positioned in or on the lighthead 30 or the support assembly 6. Further, the controller 60 may be positioned outside of the surgical environment 1. Moreover, there may be multiple controller interfaces spread throughout or outside the surgical environment 1 to allow remote operation of the controller 60. In addition, the controller 60 itself may be inaccessible, thereby requiring remote interfaces to access the controller 60.

The outer ring 31 and the central hub 32 have translucent portions enabling light to be emitted therethrough. Light is emitted from the outer ring 31 by a plurality of outer ring lighting modules 34 housed in the outer ring 31. Light is emitted from the central hub 32 by a central hub lighting module 35 housed in the central hub 32. In the illustrated embodiment, the outer ring 31 contains five outer ring lighting modules 34, and the central hub 32 contains one central hub lighting module 35.

Each of the lighting modules 34 and 35 contains a plurality of lamps 36 mounted therein. An example of a lamp 36 in accordance with the present invention is a light emitting diode. However, the lamps 36 are not limited to being light emitting diodes. The lamps 36 are best illustrated in FIG. 3. In the embodiment illustrated herein, the outer ring lighting modules 34 are arranged end to end in the outer ring 31 such that the lamps 36 extend around a center circumference of the outer ring 31. The lamps 36 contained in the lighting modules 34 and 35 are respectively oriented such that light emitted from the lamps 36 is transferred through the translucent portions of the outer ring 31 and the central hub 32.

The outer ring lighting modules 34 and the central hub lighting module 35 are removably fixed to the outer ring 31 and the central hub 33, respectively, using screws 38 or another fixing element that one having ordinary skill in the art would deem acceptable. As such, the outer ring lighting modules 34 and the central hub lighting module 35 can be removed to perform maintenance thereon. Such maintenance may include, but is not limited to, the replacement of lamps 36 or distance sensors 37 (described below) mounted within the outer ring lighting modules 34 and the central hub lighting module 35.

While the lighthead 30 illustrated herein has the outer ring 31 and the central hub 32, embodiments described herein are not limited to this functional design of the lighthead 30. For example, a lighthead is contemplated in which only one outer ring lighting module 34 is included in the outer ring 31. Alternatively, either the outer ring 31 or the central hub 32 may be omitted in the lighthead 30. The outer ring 31 and the central hub 32 may be dimensioned in various shapes and sizes. As the embodiments described herein are not limited to the functional design of the lighthead 30 and the lighting modules 34 and 35, the arrangement of the lamps 36 is limited only by the function design of the lighthead 30 and the lighting modules 34 and 35 in which the lamps 36 are mounted.

Each of the outer ring lighting modules 34 and the central hub lighting module 35 includes a distance sensor 37. In the present embodiment, since there are six lighting modules 34 and 35 contained in the lighthead 30, there are six distance sensors 37 contained in the lighthead 30 as well. However, embodiments disclosed herein are not limited thereto. For example, multiple distance sensors 37 can be respectively incorporated into each of the lighting modules 34 and 35. Conceivably, sensors not directed to distance detection that sense other variables can be incorporated into the lighting modules 34 and 35 alongside the distance sensors 37 to complement the data obtained from the distance sensors 37.

Each distance sensor 37 is configured to measure a single distance from the distance sensor 37 to a surface toward which the distance sensor 37 is pointed. Since the distance sensors 37 are respectively included in the lighting modules 34 and 35, it can be said the single distances measured by the distance sensors 37 are respectively reflective of the distances between the lighting modules 34 and 35 and the corresponding surfaces being illuminated by the lighting modules 34 and 35.

In an ideal situation, the single distances measured would be the distance from the distance sensors 37 to the work surface 51. However, the surface toward which the distance sensor 37 is pointed may not be the work surface 51. For example, after the lighthead 30 is positioned to optimally illuminate the work surface 51, the surgical staff member 53 may come between the distance sensor 37 and the work surface 51, thereby representing an abnormality. In such cases, the single distance measured would be the distance from the distance sensor 37 to the surgical staff member 53. In another example, the work surface 51 may be moved such that one of the lighting modules 34 and 35 no longer is positioned to illuminate the work surface 51. In such cases, the absence of the work surface 51 would be the abnormality, and the single distance measured would be the distance from the distance sensor 37 to the surface toward which the distance sensor 37 is newly pointed.

In any case, the single distances measured by the distance sensors 37 can be used to determine the true distance between the lighthead 30 and the work surface 51. For example, if one or more of the lighting modules 37 is illuminating an abnormality, the single distances determined by the distance sensors 37 would reflect this to be the case. Then, from the single distances, the true distance from the lighthead 30 to the work surface 51 can be calculated. The respective intensities of the light being emitted from the lighting modules 34 and 35 can then be adjusted in consideration of the true distance and the one or more abnormality distances, thereby serving to compensate for the abnormalities.

Figure 5:
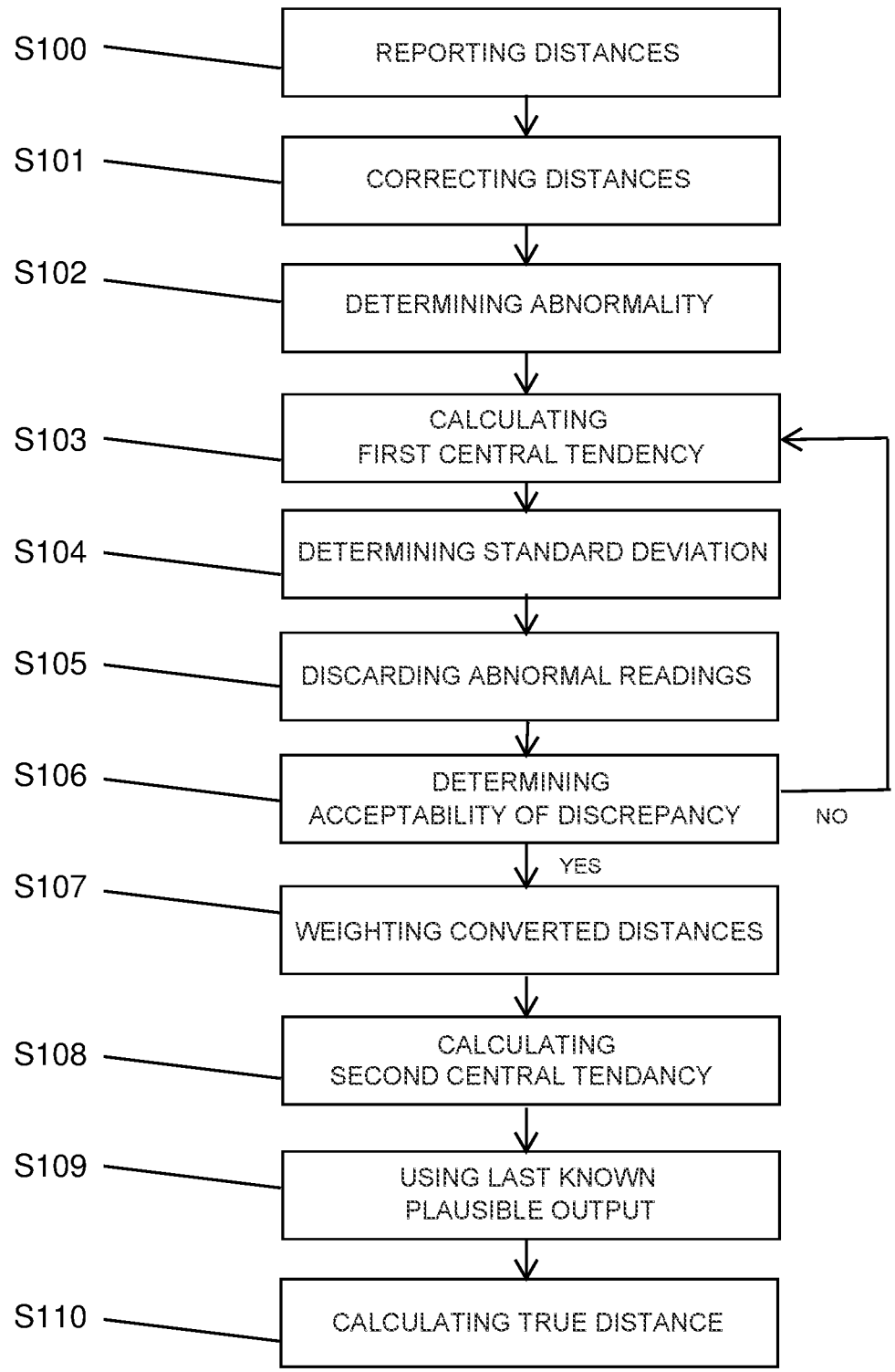
FIG. 5 is a flow diagram illustrating a method according to the first embodiment of the present invention by which a true distance between lighting modules and an illumination target is determined.

The true distance between the lighthead 30 and work surface 51 is calculated from a center of the lighthead 30. The true distance is, in fact, a representation of the distance between the center of the lighthead 30 and the surface toward which the center of the lighthead 30 is pointed. However, the true distance is determined in such a way that the surface toward which the center of the lighthead 30 is pointing is concluded to be the work surface 51. An example of how this conclusion is reached is described more specifically herebelow with reference to FIG. 5, which is a flow diagram illustrating an example method by which a true distance between the lighthead 30 and an illumination target, i.e., the work surface 51, is determined.

After each of the distance sensors 37 has measured a single distance therefrom to a surface toward which the distance sensor 37, i.e., the lighting modules 34 and 35, is pointed, each of the distance sensors 37 reports (S100) the single measured distance and a state of the single measured distance to the controller 60. The state of the single measured distance is related to the amount of time elapsed between the acquisition of the measurement data and the reporting of the measurement data to the controller 60.

In this particular case, the state of the single measured distance is determined according to a predetermined time period. If the acquired measurement is reported to the controller 60 within the predetermined time period, the state of the single measured distance is indicated to the controller 60 as being current. However, if the acquired measurement is reported to the controller 60 after the predetermined time period has expired, the state of the single measured distance is indicated to the controller 60 as being stale. A stale measurement could be a result of an inability of the distance sensor 37 to determine the single measured distance by the time at which the distance sensor 37 is required to report the measurement to the controller 60. A measurement that is stale may be a measurement that had previously been reported to the controller 60.

After the controller 60 receives the respective single measured distances for the distance sensors 37, the distances are corrected (S101) to centerline distances extending from the center of the lighthead 30 to the respective surfaces toward which the lighting modules 34 and 35 are pointed. Then, using the corrected distances, the controller 60 determines (S102) if one or more of the distance sensors 37 are subject to an out-of-range abnormality.

In this example, an out-of-range abnormality is an abnormality represented by a distance sensor 37 providing a corrected distance that, in comparison with all of the corrected distances, is either so short or so long that it could not be considered as a normal operating distance from the lighthead 30 to the work surface 51. More specifically, the distance sensors 37 are not able to specifically identify the surface to which the distance is determined. The surface may be any surface located within the surgical environment 1, including, but not limited to, the work surface 51, the surgical patient, the surgical staff member 53, other areas of the surgical table 50, or even a floor on which the surgical table 50 is positioned. A determination of an existence of an out-of-range abnormality with respect to a corrected distance would lead one to believe, i.e. the controller 60, that, when compared with all of the corrected distances, the instant corrected distance is not a distance to the work surface 51, and the light associated with the instant corrected distance is not reaching the work surface 51. In other words, the light being emitted from the lighting module 34 and 35 that includes the distance sensor 37 sensing the abnormality is not reaching the work surface 51, i.e. the illumination target. As such, when a corrected distance from a distance sensor 37 results in a determination by the controller 60 of the specific distance sensor 37 as being subject to an out-of-range abnormality, the last known good, i.e., normal, corrected measurement obtained from the distance sensor 37 is substituted as a stale measurement in place of the distance related to the measurement associated with the out-of-range abnormality.

After the determination of any out-of-range abnormalities, a first central tendency of the corrected centerline distances is calculated (S103) by condensing the distances into a first single distance output. A stale reading state is also provided by condensing the stale readings into a single stale reading. The current or stale state of the single distance output is determined based on how many of the measured distances in were current or stale. In addition, the reliability of the single measured distances is also analyzed with statistical data regarding the effect of noise of the single measured distances. Noise is a function of distance. As such, the single measured distances will contain more noise at further distances and less noise at closer distances. Thus, the reliability of the measurements is a function of the noise.

After the first central tendency is calculated, a standard deviation is determined (S104) with respect to an expected discrepancy between the single measured distances and the condensed first single distance output. Through iteration, readings of the single measured distances that are considered abnormal are discarded (S105). The single measured distances are then averaged, thereby leading to the determination (S106) of whether the expected discrepancy related to the standard deviation is acceptable. If single measured distances outside of the expected discrepancy are discarded or the averaged value falls outside the standard deviation, the first central tendency is recalculated (S103), another standard deviation is determined (S104), and additional abnormal distances are discarded (S105).

This process repeats until it is determined (S106) that no additional single measured distances are discarded in an iteration in S105 or the expected discrepancy is within acceptable limits. After such a determination, the converted distances are weighted (S107) toward a center of the lighthead 30. In the instant example, the distance sensor 37 of the central hub lighting module 35 is more likely to be aimed at the work surface 51 than the distance sensors 37 of the outer ring lighting modules 34. Further, the distance sensor 37 of the central hub lighting module 35 is less likely to experience out-of-range abnormalities than the distance sensors 37 of the outer ring lighting modules 34. As such, the converted distance of the distance sensor 37 of the central hub lighting module 35 is weighted more heavily than the converted distances of the distance sensors 37 of the outer ring lighting modules 34, as the distance sensor 37 of the central hub lighting module 35 is closer to the center of the lighthead 30. An additional weighting is also applied to reduce the weight of stale measured distances as compared with current measured distances.

A second central tendency (S108) is then calculated by condensing the measured distances are condensed into a single distance output, even if it is stale. If the single distance output is not updated, the last known plausible (or default) single distance output is used (S109). Low pass filtering is then applied to remove noise and provide a more stable value for the single distance output. A final single centerline distance—the true distance—from the lighthead 30 to the work surface 51 is then calculated (S110).

The intensity or amount of light emitted from the lighting modules 34 and 35, i.e., the lamps 36 of the lighting modules 34 and 35, is then adjusted to compensate for the detected out-of-range abnormalities to ensure that a predetermined amount of light is illuminating the work surface 51. The light being emitted from the lighting modules 34 and 35 is selectable according to whether the respective lighting modules 34 and 35 are subject to abnormalities.

For example, if an abnormality is identified through the readings reported by a distance sensor 37 in one of the outer ring lighting modules 34, the controller 60 will use the distance readings reported to predict the amount of illumination that the abnormality affected outer ring lighting module 34 is providing to the work surface 51 in view of the abnormality. The controller 60 will then use the true distance to predict the amount of illumination that should be provided to the work surface 51 if all of the lighting modules 34 and 35 are unaffected by abnormalities.

The amount or intensity of the light being emitted from the abnormality affected outer ring lighting module 34 may then be decreased. In addition, the amount or intensity of the light being emitted from the remaining outer ring lighting modules 34 and the central hub lighting modules 35 may be respectively increased by the controller 60 to compensate for the lack of illumination being provided by the abnormality affected outer ring lighting module 34. The amount of illumination compensation needed from the remaining outer ring lighting modules 34 and the central hub lighting modules 35 is determined based on the amount of illumination predicted using the true distance.

The foregoing descriptions are example embodiments of the present invention. It should be appreciated that these embodiments are described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A system for identification of abnormalities related to illumination of a target and automatic compensation therefor, the system comprising:
    a lighthead configured to illuminate the target, the lighthead comprising lighting modules that are separate and distinct from each other, each of the lighting modules being configured to emit light therefrom, each of the lighting modules comprising a distance sensor positioned therein, each of the distance sensors being configured to measure a distance from the lighting module to a surface toward which the lighting module is pointed; and
    a controller configured to identify one or more abnormalities of the measured distances, determine a true distance from the lighthead to the target based on the measured distances, predict an amount of illumination based on the true distance that would be supplied to the target without the identified abnormalities, and compensate for the identified abnormalities by respectively adjusting amounts of light emitted from the lighting modules to illuminate the target according to the predicted amount of illumination,
    wherein the abnormalities of the measured distances respectively indicate that the surfaces toward which the lighting modules related to the abnormalities are pointed are not surfaces of the target.

2. The system according to claim 1, wherein abnormalities respectively identify blockages inhibiting the lighting modules from being pointed toward the target.

3. The system according to claim 1, wherein each of the lighting modules further comprises a plurality of lamps configured to generate light for emission thereof from the lighting module, and
    wherein the controller is further configured to adjust an amount of light generated by the lamps to adjust the amount of light emitted from the lighting modules.

4. The system according to claim 1, further comprising:
    a support assembly configured to adjustably support the lighthead from a surface other than the surfaces of the target.

5. The system according to claim 4, wherein the surface from which the support assembly adjustably supports the lighthead is a ceiling of an area containing a surgical environment, and
    wherein the target is a work surface positioned in the surgical environment, the work surface being configured to support a surgical patient thereon.

6. The system according to claim 1, wherein the target is a work surface positioned within a surgical environment, the target being configured to support a surgical patient thereon.

7. The system according to claim 1, wherein the true distance is a distance between a center of the lighthead and a surface to which the center of the lighthead is pointed, and wherein the surface to which the center of the lighthead is pointed is the target.

8. The system according to claim 7, wherein the true distance is dependent upon the measured distances that are not affected by the abnormalities.

9. A method for identification of abnormalities related to illumination of a target and automatic compensation therefor, the method comprising:
respectively measuring, via distance sensors, distances from separate and distinct lighting modules of a lighthead to surfaces toward which the lighting modules are respectively pointed, each of the lighting modules being configured to emit light therefrom, each of the lighting modules including one of the distance sensors positioned therein;
identifying, via a controller, one or more abnormalities of the measured distances;
determining, via the controller, a true distance from the lighthead to the target based on the measured distances;
predicting, via the controller, an amount of illumination based on the true distance that would be supplied to the target without the identified abnormalities; and
compensating, via the controller, for the identified abnormalities by respectively adjusting amounts of light emitted from the lighting modules to illuminate the target according to the predicted amount of illumination,
wherein the abnormalities of the measured distances respectively indicate that the surfaces toward which the lighting modules related to the abnormalities are pointed are not surfaces of the target.

10. A method for identification of abnormalities related to illumination of a target and automatic compensation therefor, the method comprising:
measuring a distance from each of a plurality of lighting modules of a lighthead to a surface toward which the lighting module is pointed;
identifying, via a controller, one or more abnormalities of the measured distances;
determining, via the controller, a true distance from the lighthead to the target based on the measured distances;
predicting, via the controller, an amount of illumination based on the true distance that would supplied to the target without the identified abnormalities; and
compensating, via the controller, for the identified abnormalities by respectively adjusting an amount of light emitted from the lighting modules to illuminate the target according to the predicted amount of illumination,
wherein the abnormalities of the measured distances respectively indicate that the surfaces toward which the lighting modules related to the abnormalities are pointed are not surfaces of the target, and
wherein the determining of the true distance comprises respectively correcting the measured distances so that, the corrected distances are centerline distances extending from a center of the lighthead to the surfaces toward which the lighting modules are pointed.

11. The method according to claim 10, wherein the abnormalities are identified based on a comparison of all of the corrected distances, and
wherein one of the corrected distances is identified as an abnormality when a determination is made by the controller that, when compared with all of the corrected distances, the one of the corrected distances is not a distance to the target and light associated with the one of the corrected distances is not reading the target.

12. The method according to claim 11, wherein, when the one of the corrected distances is identified as an abnormality, a stale corrected distance previously identified as being normal is substituted therefor.

13. The method according to claim 9, wherein the compensating comprises:
decreasing an amount of light emitted from the lighting modules associated with the abnormalities; and
increasing an amount of light emitted from the lighting modules not associated with the abnormalities.

14. The method according to claim 13, wherein the amount of light emitted from the lighting modules not associated with the abnormalities is increased according to the predicted amount of illumination to compensate for a lack of light being provided by the lighting modules associated with the abnormalities.

\* \* \* \* \*